(12) United States Patent
Ko et al.

(10) Patent No.: US 9,782,431 B2
(45) Date of Patent: Oct. 10, 2017

(54) METHOD TO PREPARE HIRSUTELLA SINENSIS POLYSACCHARIDES POSSESSING ANTI-OBESITY PROPERTIES AND USES THEREOF

(71) Applicant: Chang Gung Biotechnology Corp., Taipei (TW)

(72) Inventors: Yun-Fei Ko, Taipei (TW); Jan Martel, Taipei (TW); Jian-Ching Liau, Taipei (TW); I-Te Chang, Taipei (TW); Chien-Sheng Lee, Taipei (TW); Wei-Chang Wang, Taipei (TW); Chen-Yaw Chiu, Taipei (TW); Chih-Jung Chang, Taipei (TW); Chuan-Sheng Lin, Taipei (TW); Tsung-Ru Wu, Taipei (TW); Chia-Chen Lu, Taipei (TW); David Marcelo Ojcius, Taipei (TW); Hsin-Chih Lai, Taipei (TW); Ding-E Young, Taipei (TW)

(73) Assignee: Chang Gung Biotechnology Corp., Taipei (TW)

( * ) Notice: Subject to any disclaimer, the term of this patent is extended or adjusted under 35 U.S.C. 154(b) by 18 days.

(21) Appl. No.: 14/856,397

(22) Filed: Sep. 16, 2015

(65) Prior Publication Data
US 2016/0361348 A1    Dec. 15, 2016

(30) Foreign Application Priority Data

Jun. 11, 2015   (TW) .............................. 104118926 A

(51) Int. Cl.
*A61K 31/736*   (2006.01)
*A61K 36/062*   (2006.01)
*C08B 37/00*    (2006.01)

(52) U.S. Cl.
CPC .......... *A61K 31/736* (2013.01); *A61K 36/062* (2013.01); *C08B 37/0087* (2013.01); *A61K 2236/53* (2013.01)

(58) Field of Classification Search
CPC ... A61K 31/736; A61K 36/062; A61K 36/068
See application file for complete search history.

(56) References Cited

PUBLICATIONS

Koh et al., Biol. Pharm. Bull., 2003, 26(1), pp. 84-87.*
Primordia entry for Cordyceps sinensis (Primordia World of Mushrooms website, http://www.primordiamushrooms.com/our-products/cordyceps-sinensis/, accessed online on Feb. 8, 2017.*
Klop et al., Nutrients, 2013, 5, p. 1218-1240.*
Kiho et al., Biol. Pharm. Bull., 1993, 16(12), p. 1291-1932.*

* cited by examiner

*Primary Examiner* — Jonathan S Lau
(74) *Attorney, Agent, or Firm* — WPAT, P.C., Intellectual Property Attorneys; Anthony King

(57) ABSTRACT

The present invention provides a method to prepare polysaccharides from *Hirsutella sinensis*. The prepared polysaccharides reduce body weight and fat accumulation in laboratory animals, and can therefore be used to prevent and treat obesity.

7 Claims, 9 Drawing Sheets

METHOD TO PREPARE HIRSUTELLA SINENSIS POLYSACCHARIDES POSSESSING ANTI-OBESITY PROPERTIES AND USES THEREOF

CROSS-REFERENCE TO RELATED APPLICATION

This application claims priority of Taiwan patent application No. 104118926, filed on Jun. 11, 2015, the content of which is incorporated herein in its entirety by reference.

BACKGROUND OF THE INVENTION

1. Field of the Invention

The present invention relates to compositions and methods for treating obesity. Specifically, the present invention provides methods for treating obesity using polysaccharides isolated from *Hirsutella sinensis* as well as methods to prepare the polysaccharides.

2. The Prior Art

Traditional Chinese medicine has a long history in Asian countries dating back several thousands of years. One class of traditional remedies commonly in use consists of medicinal mushrooms such as *Antrodia cinnamomea*, *Agaricus blazei* Murrill, *Ganoderma lucidum*, and *Ophiocordyceps sinensis*, which contain a wide range of immuno-modulatory and bioactive compounds. The medicinal mushroom *Ophiocordyceps sinensis* has been used for centuries to promote health and longevity. Recent work has identified that the anamorphic, mycelium form of *O. sinensis* fruiting bodies is *Hirsutella sinensis*. Previous studies have shown that extracts of *O. sinensis* fruiting bodies and *H. sinensis* mycelium produce similar beneficial effects on laboratory animals, including anti-fatigue, anti-inflammatory, kidney-protecting, and libido-enhancing effects. However, the possibility that *H. sinensis* mycelium may produce anti-obesity effects has not been explored.

Obesity is now considered a disease condition associated with numerous health problems and a reduced life expectancy. Growing evidence indicates that obesity is closely linked with chronic, low-grade inflammation which can lead to insulin resistance, type 2 diabetes, fatty liver disease, cardiovascular disease, obstructive sleep apnea, and cancer. The high prevalence of obesity represents a major threat to public health, with an estimated 500 million obese people and 1.4 billion overweight individuals worldwide. Prevention of obesity is therefore a major challenge for modern societies.

Several treatments have been used to prevent and treat obesity in the general population, including calorie restriction, low-carbohydrate diets, and regular exercise. However, these treatments are difficult to implement over a long period of time and they are associated with low patient compliance. A number of treatments, including antibiotics and prebiotics, are being evaluated for the management of obesity and its related metabolic disorders. For example, antibiotic treatment alters the gut microbiota, reduces blood endotoxemia, and improves glucose tolerance in obese mice lacking the leptin gene (ob/ob mice) or in mice fed with a high-fat diet (HFD). In addition, prebiotics represent non-digestible, fermentable polysaccharides and oligosaccharides, which reduce body weight and exert anti-inflammatory effects, mainly by enhancing the growth of specific beneficial bacteria found in the gut. Prebiotics not only alter the intestinal microbiota but also maintain intestinal tight junction integrity and decrease blood endotoxemia caused by bacterial lipopolysaccharides (LPS). Modern diets tend to incorporate high levels of refined sugars and processed foods and are low in vegetables and prebiotics which would normally help maintain body weight and general health. Therefore, there is a need for safe and easy-to-use sources of prebiotics.

In view of the growing incidence of obesity in the human population and the difficulties observed in prevention and treatment, there is a need for alternative modes of prevention, treatment and control of this condition. New measures that can be introduced in the diet without necessitating considerable changes in lifestyle and without incurring in toxicity or adverse effects are particularly needed.

SUMMARY OF THE INVENTION

A primary objective of the present invention is to provide a method for treating obesity, comprising the administration of an effective amount of a polysaccharide extracted from *H. sinensis* mycelium to an obese subject, wherein the polysaccharide is extracted with water and contains at least mannose, glucose, and galactose.

According to an embodiment of the present invention, the polysaccharide further contains fucose, rhamnose, arabinose, glucosamine, and galactosamine.

According to an embodiment of the present invention, a weight ratio of the fucose, rhamnose, arabinose, glucosamine, galactose, glucose, mannose and galactosamine in the polysaccharide ranges between 3:3:1:4:23:12:50:0.2 and 4:4:2:5:24:13:51:0.6.

According to an embodiment of the present invention, the effective daily amount or dosage of the polysaccharide given to the subject is from 0.001 mg/kg to 1 g/kg. Preferably, the effective daily amount or dosage of *H. sinensis* polysaccharide given to a human subject (with an average weight of 70 kg) is 4.53 g (0.0646 g per kilogram of body weight).

According to an embodiment of the present invention, the polysaccharide has a molecular weight ranging from 15,776 Da to 1,231,969 Da, and a polydispersity index (Mw/Mn) of 7.475, and an average molecular weight of the polysaccharide is 312 kDa.

Another objective of the present invention is to provide a method for preparing the polysaccharide extracted from *H. sinensis*, comprising: extracting *H. sinensis* mycelium with water; inducing the formation of a precipitate with an alcohol; isolating the precipitate by centrifugation; and fractionating the precipitate using filtration; wherein, (a) mixing *H. sinensis* mycelium with water to give a first mixture; extracting the first mixture for a first predetermined time under a low-speed rotation to obtain a supernatant; and concentrating the supernatant to obtain a concentrated water extract of *H. sinensis*; (b) adding an alcohol to the concentrated *H. sinensis* water extract to give a second mixture; allowing the second mixture to stand for a second predetermined time to allow formation of a precipitate; and (c) isolating the precipitate by centrifugation; and fractionating the precipitate by TFF to obtain a *H. sinensis* polysaccharide.

According to an embodiment of the present invention, for step (a), the *H. sinensis* mycelium is mixed with water at a ratio of 5% (w/v).

According to an embodiment of the present invention, for step (a), the supernatant is treated at a high temperature.

According to an embodiment of the present invention, for step (a), the supernatant is concentrated using a vacuum concentrator.

According to an embodiment of the present invention, for step (b), the alcohol is 95% ethanol.

According to an embodiment of the present invention, for step (b), each volume of the concentrated *H. sinensis* water extract is mixed with 5 volumes of 95% ethanol.

According to an embodiment of the present invention, for step (b), the second predetermined time is at least 16 hours.

According to an embodiment of the present invention, for step (c), the *H. sinensis* polysaccharide is fractionated using TFF with a 0.2-μm hollow fiber membrane and 10-to-300-kDa cassette membranes (50 cm$^2$, PES).

The present invention provides a method of treating obesity using a polysaccharide isolated from *H. sinensis*; the polysaccharide can reduce body weight, weight gain, subcutaneous adipose tissue (SAT), and fat pad weight. Therefore, the method described in the present disclosure provides a new strategy for preventing and treating obesity and its complications.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein:

FIG. 6C), and fat pad weight (FIG. 6D) are monitored. Representative fat pads are shown in FIG. 6D (top panel; scale bars, 5 mm). Results represent means±standard error of the mean (SEM). Statistical significance was analyzed using one-way ANOVA analysis (P<0.01, *P<0.001, ns, non-significant).

DETAILED DESCRIPTION OF THE PREFERRED EMBODIMENT

In the following description of the embodiments of the present invention, reference is made to the accompanying drawings, which are shown to demonstrate the specific embodiments in which the present disclosure may be practiced. These embodiments are provided to enable those skilled in the art to practice the present disclosure, and it is understood that changes can be made to the embodiments without departing from the scope of the present invention. The following description is therefore not to be considered as limiting the scope of the present invention.

Definition

The "effective dosage" or "effective amount" described in the present invention refers to the amount of *H. sinensis* polysaccharide that can reduce body weight and fat accumulation in animals and humans. The appropriate effective dosage may vary depending on the organism or individual treated but can be determined experimentally using various techniques, including a dose escalation study.

The data shown in the present disclosure represent approximated, experimental values that can vary within a range of ±20%, preferably ±10%, and most preferably ±5%.

The present invention provides a method for treating obesity, comprising: administering an effective amount of a polysaccharide sub-fraction isolated from *H. sinensis* to an obese subject. The experiments described below show the effects of the isolated polysaccharide sub-fraction on body weight and fat levels in mice fed a HFD. Generally, the polysaccharide extracted from *H. sinensis* in the present invention can be given to mammals and humans at a dose of 0.001-1,000 mg/kg of body weight per day. The details of the invention are given below.

Example 1

Preparation of *H. sinensis* Water Extracts and Polysaccharide Sub-Fractions

In the present invention, a sub-fraction of *H. sinensis* polysaccharides is described that can effectively prevent and treat obesity and reduce fat accumulation in animals and humans. The *H. sinensis* polysaccharide sub-fraction of the present invention can be added to the diet of the subject as a drink, a daily supplement, or a food, without incurring in significant lifestyle changes, toxicity, or other unfavorable effects on the subject's health.

1.1 Preparation of Water Extracts of *H. sinensis*

Figure 1:
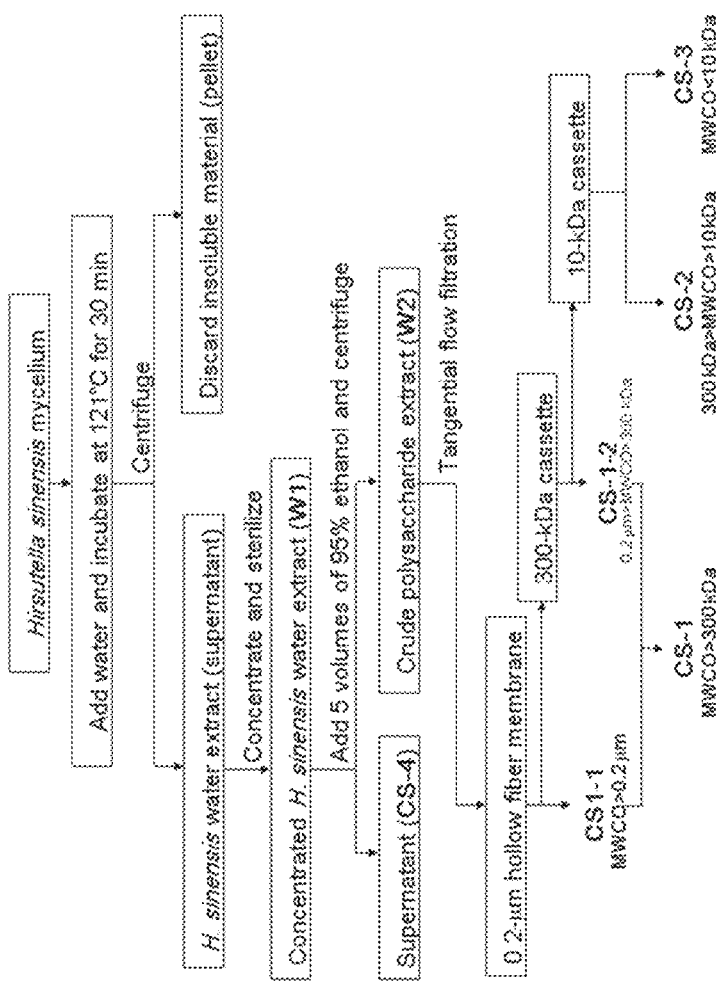
FIG. 1 shows a simplified flowchart for the isolation of *H. sinensis* water extracts and polysaccharides sub-fractions described in the present invention.

As shown in FIG. 1, a water extract is prepared by mixing 500 g of *H. sinensis* mycelium obtained from Chang Gung Biotechnology (Taipei, Taiwan) into 10 liters of distilled water using a 20 liter-stirred tank reactor to obtain a mixture. The 5% (w/v) mixture is agitated at a speed of 150 revolutions per minute (RPM) for 30 min at 121° C. The mixture is centrifuged to remove insoluble material and to obtain a water extract of *H. sinensis* (supernatant). The water extract is concentrated to a final volume of 2.5 liters using a vacuum concentrator. The concentrated supernatant is sterilized at high temperature and pressure for 20 min in an autoclave to obtain a 20% (w/v) concentrated water extract of *H. sinensis* (which is labeled W1, see FIG. 1).

1.2 Preparation of *H. sinensis* Crude Polysaccharide Extract

Referring to FIG. 1, 120 mL of 20% (w/v) the concentrated water extract of *H. sinensis* (W1, containing 2.09 g of total water-soluble carbohydrates; see Table 1) is mixed with 600 mL (1-to-5 ratio) of 95% ethanol and incubated at 4° C. for 16 hours to produce a mixture. The mixture is centrifuged to obtain a supernatant and a precipitate (pellet). The supernatant is removed, while 120 mL of 70% ice-cold ethanol is used to wash and resuspend the precipitate to give a mixture. The mixture is centrifuged to obtain a supernatant and a precipitate (pellet). The supernatants from three such washing-resuspension-centrifugation steps are combined to give a supernatant of 1,040 mL (labeled as sub-fraction CS-4, total water-soluble carbohydrate of 0.83 g; see Table 1). The crude polysaccharide extract (pellet described above) is dissolved into 1,000 mL of distilled water and concentrated to a final volume of 700 mL using a vacuum concentrator in order to remove residual ethanol. Finally, distilled water is added to obtain a crude *H. sinensis* polysaccharide extract with a final volume of 2,400 mL (labeled as sub-fraction W2, containing 1.26 g of total water-soluble polysaccharides; see Tables 1 and 2).

1.3 Fractionation of *H. sinensis* Crude Polysaccharide Extract 2,400 mL of *H. sinensis* crude polysaccharide extract is placed into a beaker and incubated at 50° C. in a water bath. The extract is fractionated using a TFF system (KrosFlo, Spectrum Laboratories) with a 0.2-μm hollow fiber membrane (1,500 cm$^2$, polyethersulfone, PES). The trans-membrane pressure (TMP) is set at 15-16 psi. 600 mL of distilled water is added into the retentate during filtration when the volume of the retentate ranges from 800 to 1,000 mL. Addition of water is repeated two times (a total of 1,800 mL distilled water is added to the retentate). A 1,250 mL retentate (labeled as CS-1-1, total water-soluble polysaccharide of 0.24 g) and 3,600 mL of filtrate are obtained this way.

The above-mentioned 3,600 mL of 0.2-μm filtrate is placed into a beaker and incubated at 50° C. in a water bath. The 3,600 mL of filtrate is fractionated using TFF with a 300-kDa cassette membrane (50 cm$^2$, PES). The TMP is set between 18-20 psi. 600 mL of distilled water is added into the retentate during filtration when the volume of the retentate ranges from 1,000 mL to 1,200 mL. 1,040 mL of retentate (labeled as CS-1-2, total water-soluble polysaccharide of 0.18 g) and 3,600-mL of filtrate are obtained. Fractions CS-1-1 and CS-1-2 are combined to obtain a volume of 2,290 mL (labeled as sub-fraction CS-1, containing 0.42 g of total water-soluble polysaccharides; see Table 2).

The above-mentioned 3,600 mL of 300-kDa filtrate is placed into a beaker and incubated at 50° C. in a water bath. The 300-kDa filtrate is fractionated using TFF with a 10-kDa cassette membrane (50 cm$^2$, PES). The TMP is set between 18-20 psi. 600 mL of distilled water is added into the retentate during filtration when the volume of the retentate ranges from 1,000 mL to 1,200 mL. The operation is repeated to obtain 990 mL of 10-kDa-to-300 kDa retentate (labeled as sub-fraction CS-2, total water soluble-polysaccharides of 0.64 g; see Table 2) and 3,600 mL of 10 kDa filtrate (labeled as sub-fraction CS-3, total water-soluble polysaccharides of 0.16 g; see Table 2). The CS-1, CS-2, CS-3 and CS-4 sub-fractions are concentrated separately using the vacuum concentrator to obtain a final volume of 120 mL. Concentrated fractions are sterilized at high temperature and pressure in an autoclave for 20 min.

1.4 Determination of Total Water-Soluble Carbohydrates and Polysaccharides in Water Extracts and Polysaccharide Sub-Fractions Isolated from *H. sinensis*

The phenol-sulfuric acid assay is used to determine the level of total water-soluble carbohydrates and polysaccharides in the extracts and sub-fractions isolated from *H. sinensis*, which comprise: 20% (w/v) the *H. sinensis* water extract (labeled as W1; 120 mL), the *H. sinensis* crude polysaccharide extract (labeled as W2; 2,400 mL), a combination of the retentate of the 0.2-μm filtration step and the 300-kDa-cutoff pore filtration (labeled as CS-1 sub-fraction; 2,290 mL), the retentate of the 10-kDa membrane filtration (labeled as CS-2 sub-fraction; 990 mL), the filtrate of the 10-kDa-cutoff membrane filtration (labeled as CS-3 sub-fraction; 3,600 mL), and the supernatants obtained after precipitation induced by addition of 95% ethanol (labeled as CS-4 sub-fraction; 1,040 mL). To establish a standard curve for the phenol-sulfuric acid assay, glucose standard solutions are prepared at concentrations of 0, 0.02, 0.04, 0.06, 0.08, 0.10, 0.12, 0.14, 0.16, 0.18, and 0.20 mg/mL. 200 μL of each solution is placed into 1.5-mL tubes. 200 μL of 5% phenol is added and the solution is mixed. 1 mL of sulfuric acid is added and the solution is mixed. After incubation for 20 min, absorbance at 490 nm is monitored using a spectrophotometer to obtain the calibration curve of standard glucose solutions (calculated $R^2 > 0.99$). After appropriate dilution of the sample solutions, 200 μL of each diluted sample solution is placed into 1.5-mL tubes. Phenol and sulfuric acid are added as above and absorbance is measured. The values obtained are plotted onto the calibration curve to determine the concentration of total water-soluble carbohydrates or polysaccharide of the samples.

Total water-soluble carbohydrates and polysaccharides found in the water extracts and polysaccharide sub-fractions isolated from *H. sinensis* are shown in Tables 1 and 2, which show that the W2 crude polysaccharide extract contains 0.42 g of water-soluble polysaccharides with a molecular weight above 300 kDa (CS-1), which accounts for 33.3% of total polysaccharides found in the W2 crude extract. The W2 crude polysaccharide extract also contains 0.64 g of polysaccharides with a molecular weight between 10 kDa and 300 kDa (CS-2), which accounts for 50.8% of the total polysaccharides found in the W2 crude polysaccharide extract. Finally, the W2 extract contains 0.16 g of carbohydrates with a molecular weight lower than 10 kDa (CS-3), which accounts for 12.7% of total carbohydrates found in the W2 extract.

TABLE 1

Water-soluble carbohydrates and polysaccharides found in the extracts and sub-fractions isolated from *H. sinensis*

| Fraction | | Content (g) | Percentage (%) |
|---|---|---|---|
| W1 | Total water-soluble carbohydrates | 2.09 | 100 |
| W2 | Total water-soluble polysaccharides | 1.26 | 60.3 |
| CS-4 | Mono-, di-, oligo-saccharides | 0.83 | 39.7 |

TABLE 2

Polysaccharide distribution of the crude *H. sinensis* polysaccharide extract (W2)

| Fraction | | Content (g) | Percentage (%) |
|---|---|---|---|
| W2 | Total water-soluble carbohydrates | 1.26 | 100 |
| CS-1 | MWCO > 300 kDa | 0.42 | 33.3 |
| CS-2 | 300 kDa > MWCO > 10 kDa | 0.64 | 50.8 |
| CS-3 | 10 kDa > MWCO | 0.16 | 12.7 |

MWCO: molecular weight cut-off 1.5 Monosaccharide Analysis of CS-1 Polysaccharide Sub-Fraction Isolated from *H. sinensis*

High pH anion exchange chromatography-pulsed amperometric detection (HPAEC-PAD) is used to analyze the monosaccharide composition of the CS-1 sub-fraction, which is selected here for further analysis. Monosaccharide standard solutions of L-fucose, L-rhamnose, D-galactosamine, D-arabinose, D-glucosamine, D-galactose, D-glucose and D-mannose are prepared at concentrations of 0.1, 0.5, 1, 2, and 5 mg/L. 25 μL of each solution is used for ionic chromatography analysis with the HPAEC-PAD Dionex ICS-5000 system (CarboPacPA1 column with an internal diameter of 4×250 mm, Thermo Scientific). Elution is performed with 16 mM NaOH (which corresponds to a mixture of water and 200 mM NaOH at a volume ratio of 92:8) and the flow rate is 1 mL/min. The temperature of the column is set at 30° C. After 30 min of analysis, peak area of each monosaccharide standard is determined at 0.1, 0.5, 1, 2, and 5 mg/L. The standard curve of monosaccharide standards is established ($R^2 > 0.99$).

Figure 2:
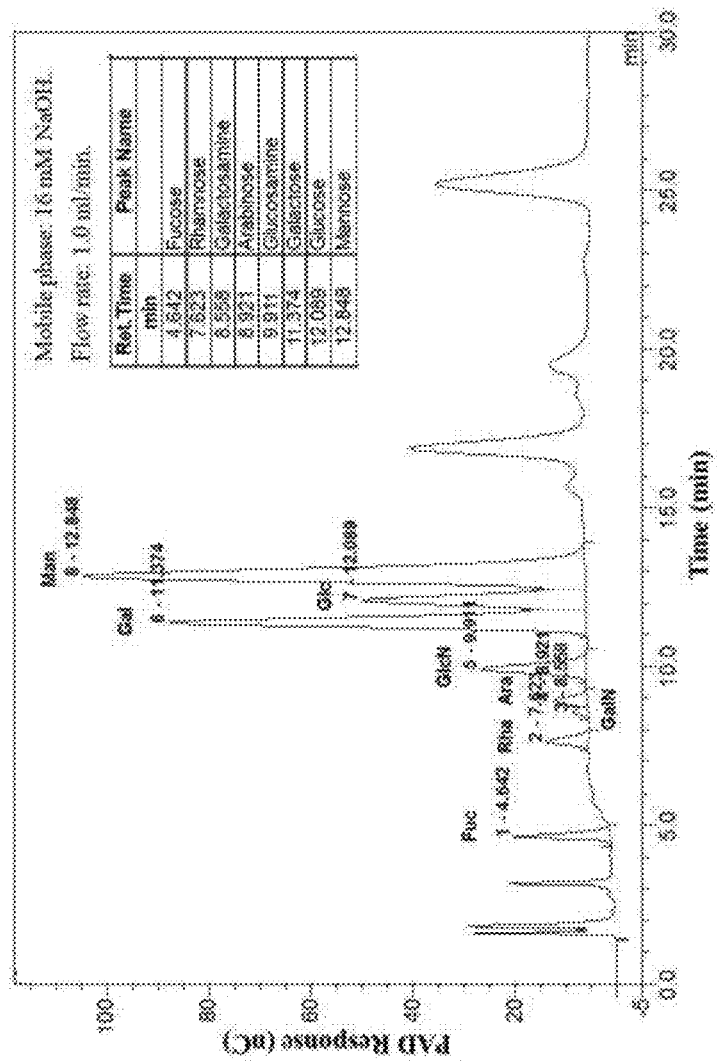
FIG. 2 shows the monosaccharide analysis of *H. sinensis* polysaccharide sub-fraction CS-1 described in the present invention. The analysis is performed using high-performance anion exchange chromatography with pulsed amperometric detection (HPAEC-PAD).

1 mL of CS-1 sub-fraction (3 mg of total water-soluble polysaccharides) is hydrolyzed with 1.79 mL of distilled water and 1.33 mL of trifluoroacetic acid at 112° C. in a sealed tube for 12 hours. The acid is removed by co-distillation with water after hydrolysis is completed. Each hydrolysate (1 mg) is dissolved in pure water (1 mg/mL). After a 4-fold dilution of the hydrolysate with pure water (0.25 mg/mL), 25 μL of the hydrolysate solution is used for ionic chromatography-HPAEC-PAD analysis. Elution is performed with 16 mM NaOH as described above. After 30 min of analysis, the analytic HPAEC-PAD profile of the hydrolysate solution is acquired. The monosaccharide composition and molar ratio of the CS-1 sub-fraction is determined by comparison with the standard curve. The CS-1 sub-fraction contains 3.2% fucose, 3.4% rhamnose, 1.7% arabinose, 4.6% glucosamine, 23.8% galactose, 12.5% glucose, 50.4% mannose, and 0.4% galactosamine (Tables 3 and 4 and FIG. 2).

TABLE 3

Monosaccharide composition of the CS-1 polysaccharide sub-fraction isolated from *H. sinensis*

| Monosaccharide | Percentage (%) |
|---|---|
| Fucose | 3.2 |
| Rhamnose | 3.4 |
| Arabinose | 1.7 |
| Glucosamine | 4.6 |
| Galactose | 23.8 |
| Glucose | 12.5 |
| Mannose | 50.4 |
| Galactosamine | 0.4 |

TABLE 4

Monosaccharide molar ratio of the CS-1 polysaccharide sub-fraction isolated from *H. sinensis*

| Monosaccharide | Molar ratio |
|---|---|
| Fucose | 0.07 |
| Rhamnose | 0.07 |
| Arabinose | 0.04 |
| Glucosamine | 0.09 |
| Galactose | 0.47 |
| Glucose | 0.25 |
| Mannose | 1 |
| Galactosamine | 0.01 |

1.6 Molecular Weight Distribution of the CS-1 and CS-2 Polysaccharide Sub-Fractions Isolated from *H. sinensis*

The molecular weight of the isolated CS-1 polysaccharide sub-fraction is analyzed using size-exclusion chromatography (SEC) and high performance liquid chromatography with a refractive index (RI) detector (model 2410, Waters) and light scattering (LS) detector (model 270 dual detector, Viscotek). Dextran 670 (667,800 Da) at 1.5 mg/mL is used as standard marker to calibrate the system. 100 μL of sample is analyzed on two connected GPC columns (TSKgel G5000PWxL and TSKgel G6000PWxL; 7.8×300 mm). Elution is performed with 0.02% $NaNO_3$ in pure water and the flow rate is set at 0.5 mL/min (column temperature of 45° C.).

The molecular weight of the CS-1 polysaccharide sub-fraction is analyzed using the OmniSEC software (Viscotek) and the following equations:

Mn: number average molecular weight $$Mn = \frac{\sum NiMi}{\sum Ni}$$

Mw: weight average molecular weight $$Mw = \frac{\sum NiMi^2}{\sum NiMi}$$

Mz: higher average molecular weight $$Mz = \frac{\sum NiMi^3}{\sum NiMi^2}$$

Figure 3:
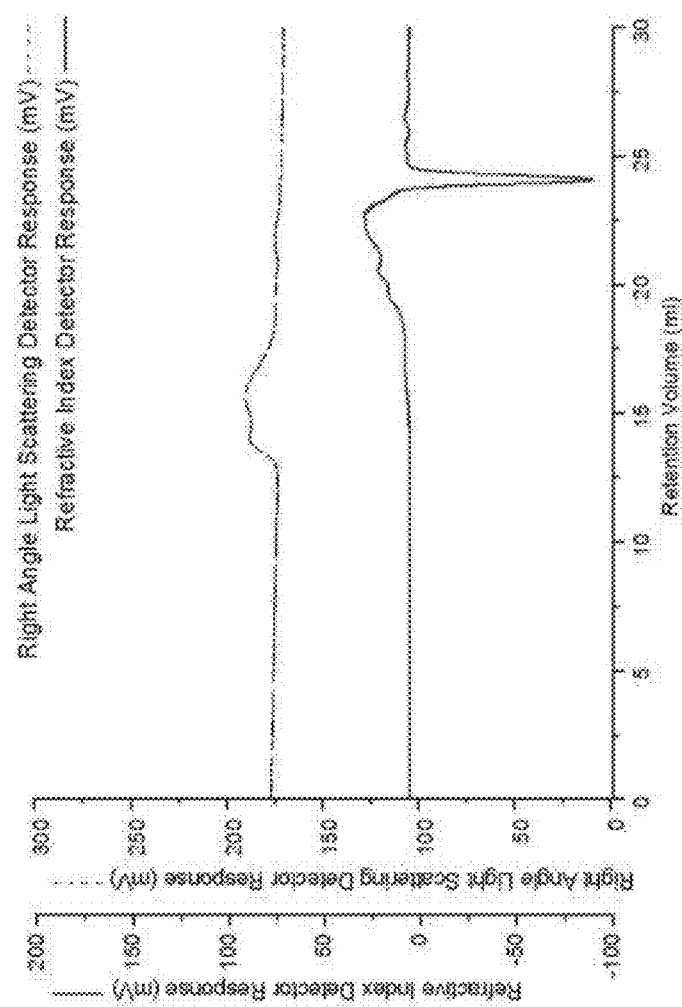
FIG. 3 shows the gel permeation chromatogram of *H. sinensis* polysaccharide sub-fraction CS-1 described in the present invention.
Figure 4:
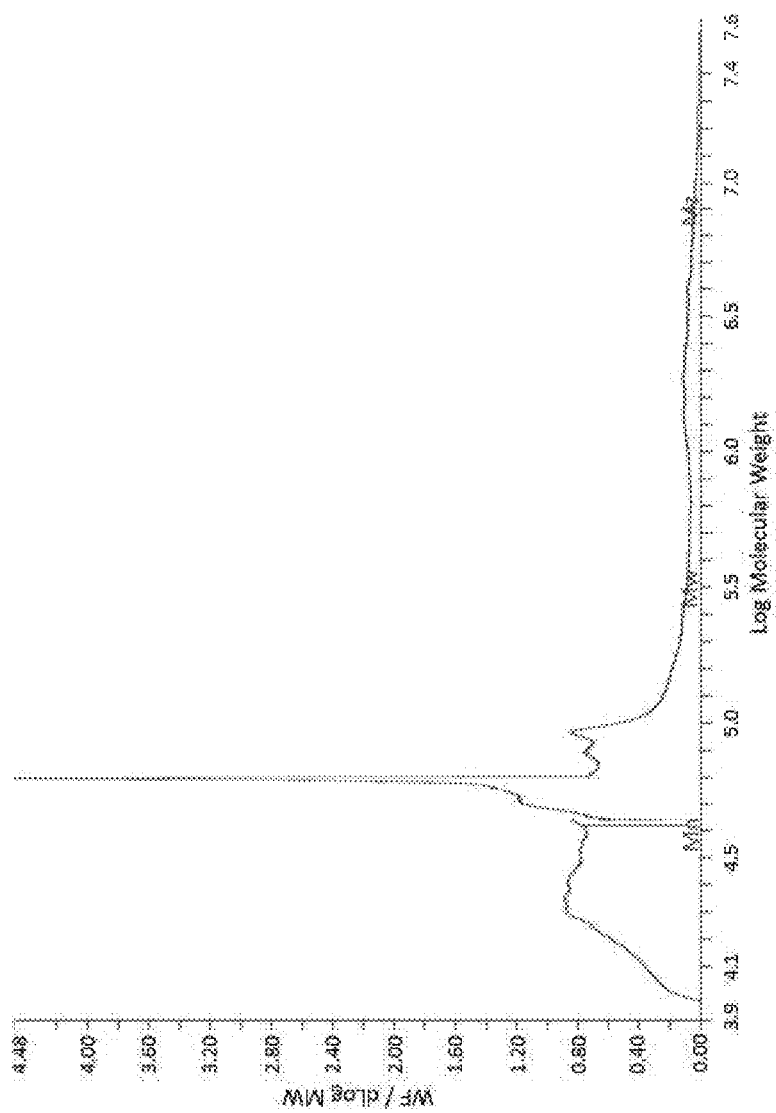
FIG. 4 shows the graph of weight fraction (WF)/dLog molecular weight (MW) vs. log molecular weight of *H. sinensis* polysaccharide sub-fraction CS-1 of the present invention.
Figure 5:
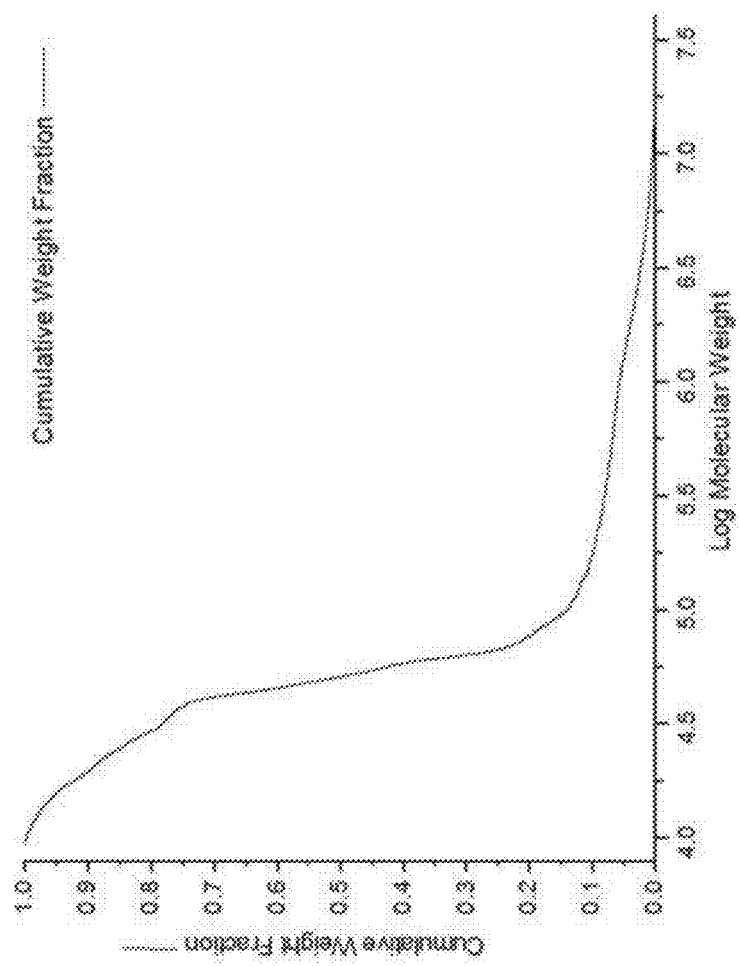
FIG. 5 shows the graph of cumulative weight fraction vs. log molecular weight of *H. sinensis* polysaccharide sub-fraction CS-1.

Mp: molecular weight at peak maximum, which is measured at the point of the molecular weight distribution maximum Mi: molecular weight of a chain Ni: number of chains of that molecular weight Analysis of the CS-1 sub-fraction (4 mg/mL of total water-soluble polysaccharides) using the GPC/SEC system and the RI and LS detectors is shown in FIG. 3. The molecular weight distribution of the polysaccharide is calculated using the Viscotek OmniSEC software (FIG. 4) and the cumulative weight fraction is determined (FIG. 5).

The cumulative weight fraction values of the CS-1 sub-fraction at 0.95 (5%) and 0.05 (95%) correspond to molecular weights of 15,776 Da and 1,231,969 Da, respectively. The polysaccharide fraction between 15,776 Da and 1,231,969 Da represents approximately 90% of the total polysaccharide weight. The polydispersity index (Mw/Mn) is measured as 7.475. Table 5 shows a comparison of the molecular weight for the CS-1 and CS-2 polysaccharide sub-fractions.

TABLE 5

Molecular weight comparison of the CS-1 and CS-2 sub-fractions

| Parameter | CS-1 | CS-2 |
|---|---|---|
| Mn (Daltons) | 41,731 | 38,842 |
| Mw (Daltons) | 311,921 | 49,215 |
| Mz (Daltons) | 7,589,000 | 79,949 |
| Mw/Mn (Polydispersity index) | 7.475 | 1.267 |
| MW of 5% of cumulative WF (Daltons) | 15,776 | 22,563 |
| MW of 95% of cumulative WF (Daltons) | 1,231,969 | 109,219 |

MW: molecular weight
WF: weight fraction

Example 2

Effects of *H. sinensis* Polysaccharide Sub-Fractions on Body Weight and Fat Accumulation in HFD-Fed Mice C57BL/6NCrlBltw mice are fed with either standard chow (13.5% of energy from fat) as control group (Chow) or HFD (60% of energy from fat) as experimental group. The mice are also treated daily with 100 μL of polysaccharide sub-fraction (CS-1, CS-2, CS-3, or CS-4) or distilled water by intragastric gavage for three months (n=10 mice for each group). The mouse groups consist of the following: HFD+CS-1, HFD+CS-2, HFD+CS-3, HFD+CS-4, HFD, Chow+CS-1, Chow+CS-2, Chow+CS-3, Chow+CS-4, and Chow.

Figure 6A:
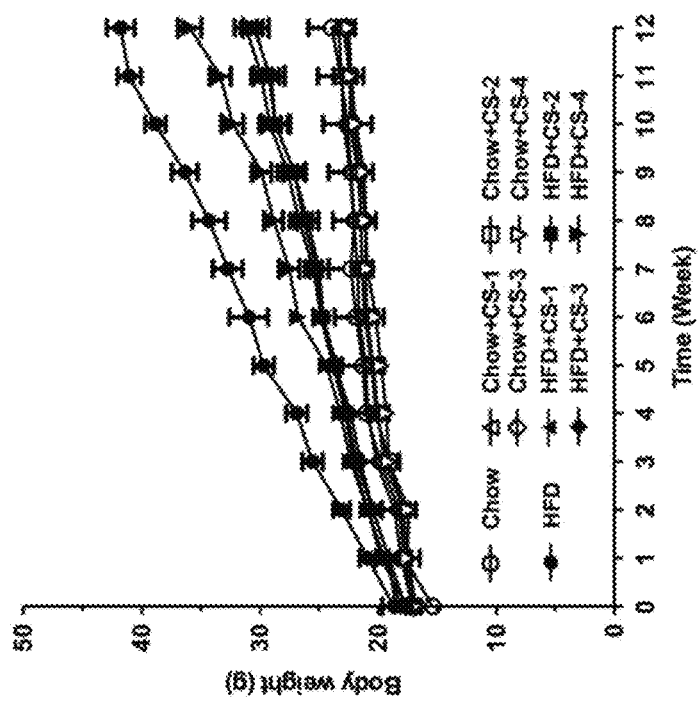
FIGS. 6A to 6D show the effects of *H. sinensis* polysaccharide sub-fractions on body weight and fat levels of mice fed with either standard chow or a HFD. Male C57BL/6 (n=10) are fed with normal chow (13.5% of energy from fat) or HFD (60% of energy from fat) plus daily administration of 100 μL of a polysaccharide sub-fraction (CS-1, CS-2, CS-3, or CS-4) or double-distilled water for 3 months by intragastric gavage. Body weight (FIG. 6A), weight gain (FIG. 6B), subcutaneous adipose tissue (SAT.
Figure 6B:
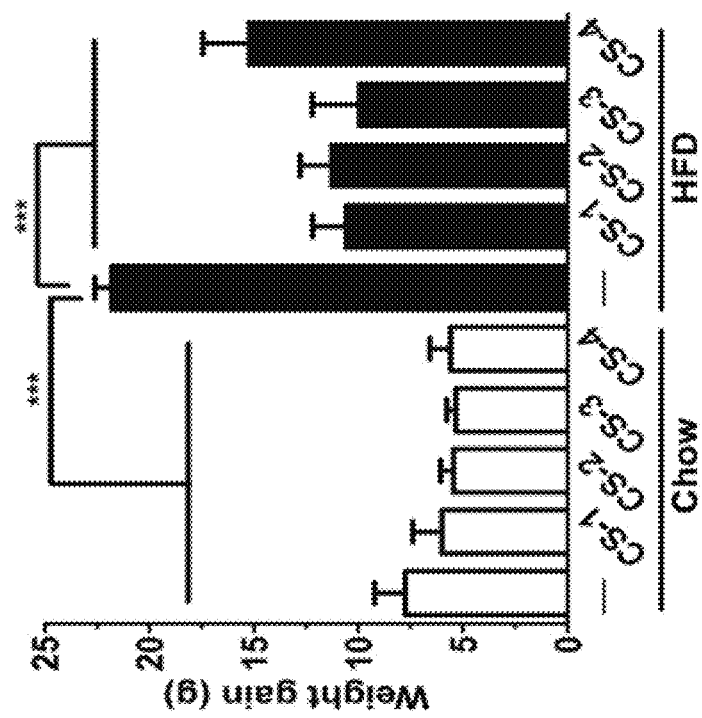
Figure 6C:
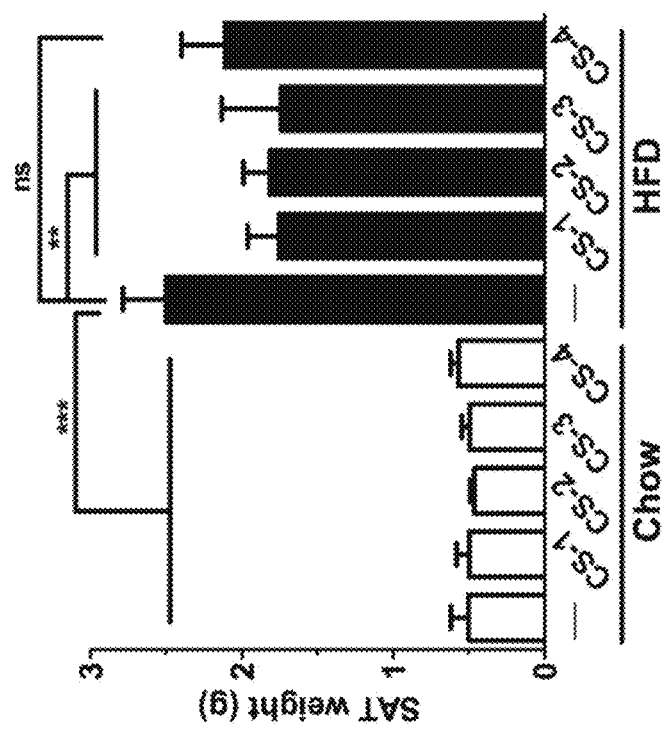
Figure 6C:
Figure 6D:
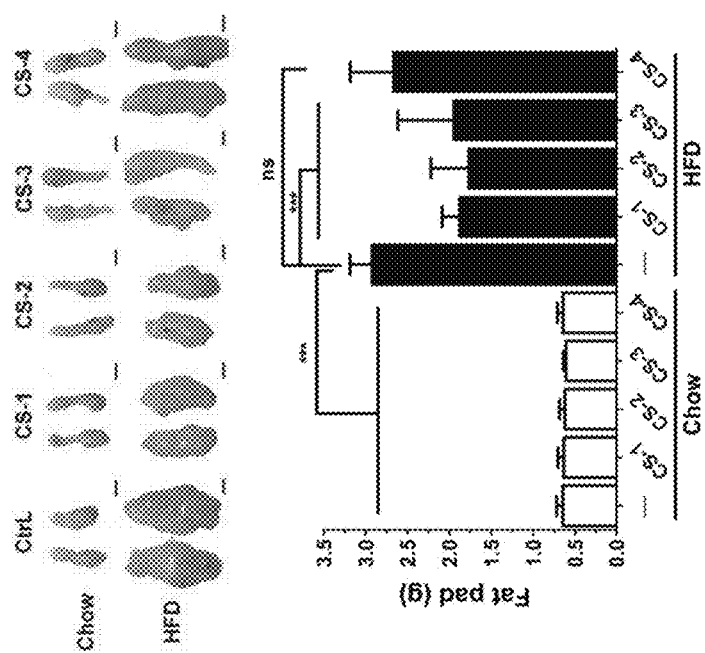

As shown in FIGS. 6A to 6D, HFD feeding increases body weight, weight gain, subcutaneous adipose tissue (SAT) weight, and fat pad weight compared to control chow feeding. Notably, the polysaccharide sub-fractions CS-1, CS-2 and CD-3 reduce body weight and fat accumulation compared to the control HFD group (FIGS. 6A-6D). The CS-4 sub-fraction significantly reduces body weight and weight gain (FIGS. 6A and 6B) but this sub-fraction does not affect fat accumulation in a statistical manner (FIGS. 6C and 6D). Based on these results, we conclude that polysaccharide sub-fractions CS-1, CS-2, and CS-3 reduce body weight, weight gain, and fat accumulation in obese mice.

Based on the results shown in FIG. 6A-6D, we can estimate the effective amount of polysaccharide that produces anti-obesity effects in a human individual, when administered daily for three months. Given that 100 μL of *H. sinensis* polysaccharide sub-fraction was given to each mouse (30 g of body weight in average), and that the CS-1 sub-fraction contains 0.35 g/100 mL, CS-2 contains 0.53 g/100 mL, and CS-3 contains 0.13 g/100 mL, we calculate that sub-fractions CS-1, CS-2 and CS-3 produce anti-obesity effects at 0.00035 g/mouse (CS-1), 0.00053 g/mouse (CS-2), and 0.00013 g/mouse (CS-3). For an average human weighing 70 kg, the effective amount is 0.82 g/human (CS-1), 1.24 g/human (CS-2), and 0.30 g/human (CS-3). In other words, the equivalent dosages of *H. sinensis* polysaccharide sub-fractions are 0.012 g/kg (CS-1), 0.018 g/kg (CS-2), and 0.0043 g/kg (CS-3).

The present invention provides a method for treating obesity by using *H. sinensis* polysaccharides and a method for preparing the *H. sinensis* polysaccharides having anti-obesity properties. The *H. sinensis* polysaccharides of the present invention can reduce body weight and fat accumulation in animals and humans. Accordingly, the present invention provides a new strategy to reduce obesity and induce weight loss in humans. The present invention has obvious potential commercial applications given the vast amount of products and treatments available to reduce body weight and maintain optimal health and well-being.

Although the present invention has been described with reference to the preferred embodiments, it will be apparent to those skilled in the art that a variety of modifications and changes may be made without departing from the scope of the present invention which is intended to be defined by the appended claims.

What is claimed is:

1. A method for treating obesity, comprising administering an effective amount of a polysaccharide extracted from *Hirsutella sinensis* to a subject in need thereof, wherein the polysaccharide is isolated from a water extract of *H. sinensis* mycelium and contains at least mannose, glucose, and galactose;
    wherein treating obesity consists of reducing body weight, body weight gain and fat accumulation.

2. The method according to claim 1, wherein the polysaccharide further contains fucose, rhamnose, arabinose, glucosamine, and galactosamine.

3. The method according to claim 2, wherein a weight ratio of the fucose, rhamnose, arabinose, glucosamine, galactose, glucose, mannose, and galactosamine in the polysaccharide ranges from 3:3:1:4:23:12:50:0.2 to 4:4:2:5:24:13:51:0.6.

4. The method according to claim 1, wherein the effective amount of the polysaccharide given to the subject ranges from 0.001 mg/kg to 1 g/kg.

5. The method according to claim 1, wherein the polysaccharide has a molecular weight ranging from 15,776 Da to 1,231,969 Da, and a polydispersity index (Mw/Mn) of 7.475.

6. The method according to claim 1, wherein an average molecular weight of the polysaccharide is 312 kDa.

7. The method according to claim 1, wherein the effective amount of the polysaccharide is 0.0646 g per kilogram of body weight.

* * * * *